(12) United States Patent  
Fujita

(10) Patent No.: US 7,588,534 B2  
(45) Date of Patent: Sep. 15, 2009

(54) ENDOSCOPE SYSTEM FOR OPERATING MEDICAL DEVICE BY VOICE

(75) Inventor: Masaya Fujita, Sagamihara (JP)

(73) Assignee: Olympus Corporation, Tokyo (JP)

(*) Notice: Subject to any disclaimer, the term of this patent is extended or adjusted under 35 U.S.C. 154(b) by 279 days.

(21) Appl. No.: 10/799,795

(22) Filed: Mar. 12, 2004

(65) Prior Publication Data

US 2005/0256370 A1 Nov. 17, 2005

(30) Foreign Application Priority Data

Mar. 14, 2003 (JP) ............................. 2003-069903

(51) Int. Cl.
*A61B 1/00* (2006.01)
*A61B 1/04* (2006.01)
(52) U.S. Cl. ...................... 600/104; 600/118
(58) Field of Classification Search ................ 600/101, 600/117, 118; 606/1; 704/275
See application file for complete search history.

(56) References Cited

U.S. PATENT DOCUMENTS 6,278,975 B1 *  8/2001   Brant et al. ................. 704/275
6,402,714 B1 *  6/2002   Kraft-Kivikoski ............ 604/23
6,911,916 B1 *  6/2005   Wang et al. ................. 340/825
2003/0139789 A1 *  7/2003   Tvinnereim et al. ........... 607/99

FOREIGN PATENT DOCUMENTS

JP         2002-336184         11/2002

* cited by examiner

*Primary Examiner*—John P Leubecker
*Assistant Examiner*—Philip R Smith
(74) *Attorney, Agent, or Firm*—Scully, Scott, Murphy & Presser, P.C.

(57) ABSTRACT

In an endoscope system according to the present invention, a system controller includes a communication I/F, a display I/F, a voice recognizing circuit which recognizes a voice signal from a microphone, a remote control I/F which receives and transmits data to/from a remote controller, a voice synthesizing circuit which synthesizes voice and generates the voice from a speaker, and an intensive operating panel I/F which receives and transmits the data to/from an intensive operating panel. An external recording medium can be connected to the system controller. A CPU can record and read image data to the external recording medium. With the structure, the device can be operated by the voice for natural conversation.

14 Claims, 8 Drawing Sheets

ENDOSCOPE SYSTEM FOR OPERATING MEDICAL DEVICE BY VOICE

This application claims benefit of Japanese Application No. 2003-069903 filed in Japan on Mar. 14, 2003, the contents of which are incorporated by this reference.

BACKGROUND OF THE INVENTION

1. Field of the Invention

The present invention relates to an endoscope system, and more particularly, to an endoscope system which is characterized by a voice operating portion for operating a device by voice.

2. Related Art Statement

Recently, a surgery is performed by using an endoscope. In the surgery using the endoscope, various treatments are executed while observing an image with the endoscope by adding, to the above-mentioned device, a gas insufflator used for inflating the abdominal cavity and an operating device such as a high-frequency cauter device for removing or clotting the living tissue as a treatment device for manual operation.

In order to easily operate and control a plurality of devices and improve the operability of an endoscope operating system having the plurality of devices, the endoscope operation system comprises: a display panel, e.g., a liquid crystal panel, as display means which is used by an operator to confirm a setting state of devices at a sterilized area; a remote operating device, e.g., a remote controller, as remote control means which is operated by the operator at a sterilized area and changes a function or set value of devices; an intensive operating panel having, on a touch panel thereof, an operating switch of the respective devices which is operated by an assistant such as a nurse at a non-sterilized area in accordance with an instruction of the operator to change the function or set value of devices; and a microphone for operating the devices by voice.

Japanese Unexamined Patent Application Publication No. 2002-336184 discloses one of the above-mentioned endoscope systems. In the endoscope system, the devices are operated by voice by vocalizing a predetermined operating command for operation.

OBJECTS AND SUMMARY OF THE INVENTION

It is an object of the present invention to provide an endoscope system which can be operated by voice for natural conversation.

According to the present invention, an endoscope system comprises:

a voice input unit which inputs voice;

a voice and character converting step which recognizes the voice inputted and converts the inputted voice into character data;

a monitoring unit which monitors command character trains for a plurality of devices that are hierarchized and are previously stored in a memory in a system controller for controlling the plurality of devices and the character data that is converted by the voice and character converting step; and an executing unit which executes an instruction previously allocated to the combination of the command character trains, upon detecting, in the converted character data, the command character train from the plurality of command character trains for a predetermined time interval in accordance with the preset hierarchy.

Other features and advantages of the present invention will apparently be understood by the following description.

BRIEF DESCRIPTION OF THE DRAWINGS

FIG. 1 is a diagram showing the entire structure of an endoscope surgery system;

FIG. 2 is a block diagram showing a connecting relationship of devices in the endoscope surgery system shown in FIG. 1;

FIG. 3 is a block diagram showing the structure of a voice recognizing circuit shown in FIG. 2;

FIG. 4 is a first flowchart showing the flow of voice control by a system controller shown in FIG. 2;

FIG. 5 is a second flowchart showing the flow of voice control by the system controller shown in FIG. 2; and FIG. 6 is a flowchart showing a modification of the flow of voice control by the system controller shown in FIG. 2;

FIG. 7 is a block diagram showing the structure of a voice recognizing circuit; and FIG. 8 is a flowchart showing the voice control processing using the voice recognizing circuit shown in FIG. 7.

DETAILED DESCRIPTION OF THE PREFERRED EMBODIMENTS

First Embodiment (Structure)

Figure 1:
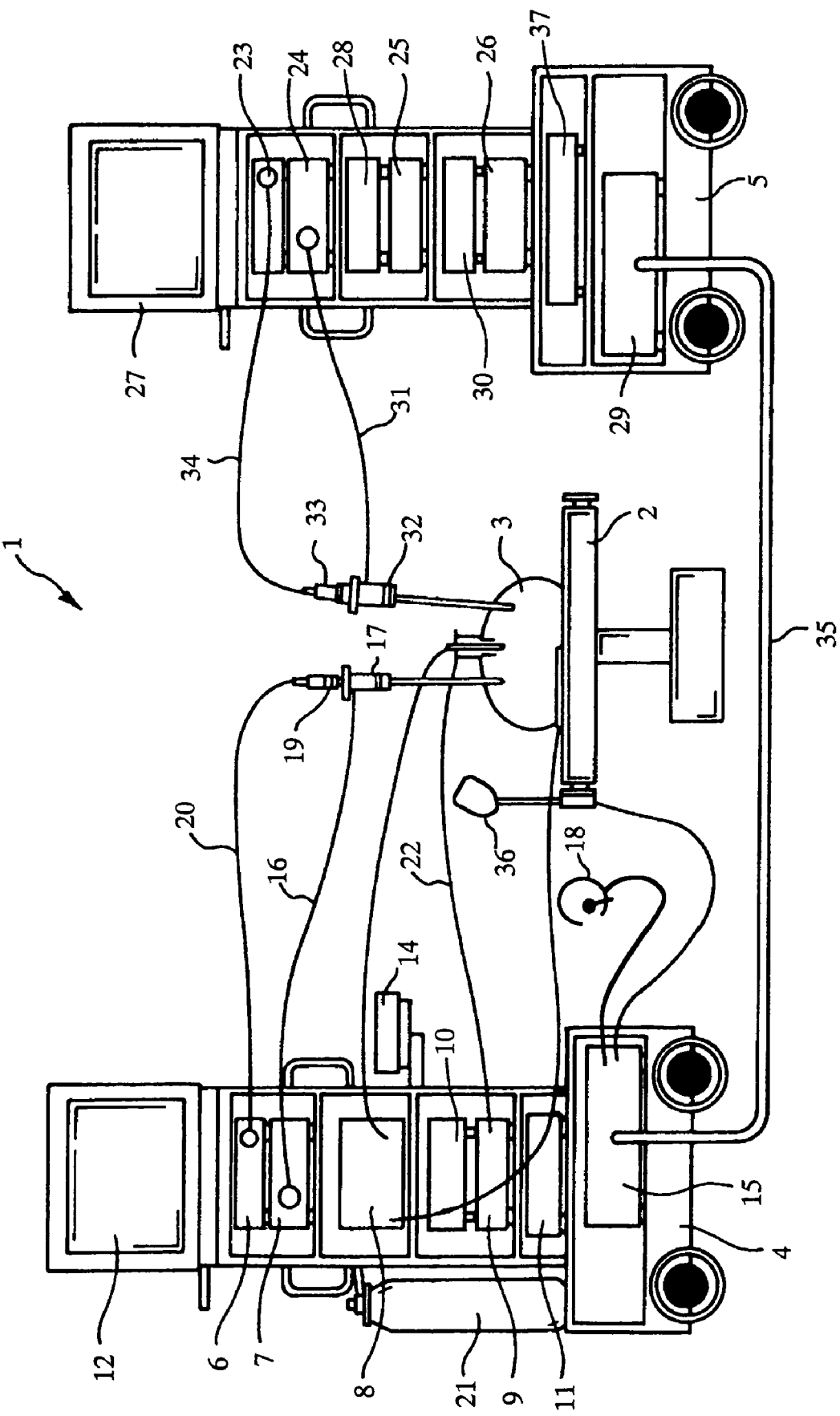
FIGS. 1 to 6 relate to a first embodiment of the present invention.

Referring to FIG. 1, an endoscope surgery system 1 as an endoscope system according to a first embodiment comprises a first trolley 4 and a second trolley 5 which are arranged on both sides of an operating table 2 on which a patient 3 is laid. The first trolley 4 and the second trolley 5 have a plurality of endoscope peripheral devices which observe, treat, and records images.

The first trolley 4 comprises: a first TV camera device 6; a first light source device 7; a high-frequency cauter device (hereinafter, referred to as an electric cautery) 8; a gas insufflator 9; an ultrasonic observing device 10; a printer 11; a first monitor 12; an intensive operating panel 14 having a pointing device, such as a mouse and a touch panel (not shown), which is arranged at a non-sterilized area and which intensively performs the operation of medical devices by a nurse; a system controller 15; and the like. The devices are connected to the system controller 15 via serial interface cables (not shown) for interactive communication. A microphone 18 is connected to the system controller 15 and the system controller 15 recognizes voice inputted from the microphone 18 by a voice recognizing circuit 46 (refer to FIG. 2), which will be described later, thus controls the devices by the operator's voice.

The first light source device 7 is connected to an first endoscope 17 via a light guide cable 16 for transmitting illumination light, supplies the illumination light from the first light source device 7 to a light guide of the first endoscope 17, and illuminates the affected part or the like in the abdominal area of the patient 3 into which an inserting portion of the first endoscope 17 is inserted.

A first camera head 19 having an image pick-up device is attached to an eyepiece portion of the first endoscope 17, an optical image of the affected part or the like through an observation optical system of the first endoscope 17 is picked up by the image pick-up device in the first camera head 19, and the image is transmitted to the first TV camera device 6 via a camera cable 20, the transmitted image is subjected to the signal processing by a signal processing circuit in the first TV camera device 6, a video signal is generated, the signal is outputted to the first monitor 12 via the system controller 15, and an endoscope image of the affected part or the like is displayed.

The system controller 15 includes an external medium recording device such as an MO (not shown), and the image recorded in the external recording medium (MO) is outputted to the first monitor 12 and displayed thereon.

The system controller 15 is connected to an in-hospital network arranged in a hospital (not shown) by a cable (not shown), and image data on the in-hospital network is outputted to the first monitor 12 and displayed thereon.

A $CO_2$ tank 21 is connected to the gas insufflator 9 so as to supply $CO_2$ gas in the abdominal area of the patient 3 via a gas insufflating tube 22 extended to the patient 3 from the gas insufflator 9.

The second trolley 5 comprises: a second TV camera device 23; a second light source device 24; an ultrasonic treatment device 25; a VTR 26; a second monitor 27; a lithotriptor 28: a pump 37; a shaver 30; and a relay unit 29 or the like. The devices are connected to the relay unit 29 by cables (not shown) for interactive communication.

The second light source device 24 is connected to a second endoscope 32 via a light guide cable 31 for transmitting the illumination light, the illumination light from the second light source device 24 is supplied to a light guide of the second endoscope 32, and the affected area or the like in the abdominal area of the patient 3, into which an inserting portion of the second endoscope 32 is inserted, is illuminated.

A second camera head 33 having an image pick-up device is attached to an eyepiece portion of the second endoscope 32. An optical image of the affected part or the like formed by an observation optical system in the second endoscope 32 is picked up by the image pick-up device in the second camera head 33, and the image is transmitted to the second TV camera device 23 via a camera cable 34, the image is subjected to the signal processing by a signal processing circuit in the second TV camera device 23, a video signal is generated, the generated signal is outputted to the second monitor 27, and an endoscope image of the affected part is displayed.

The system controller 15 and the relay unit 29 are connected by a system cable 35.

Further, a remote controller for operator (hereinafter, referred to as the remote controller 36) by which the operator operates the devices from the sterilized area is connected to the system controller 15.

Figure 2:
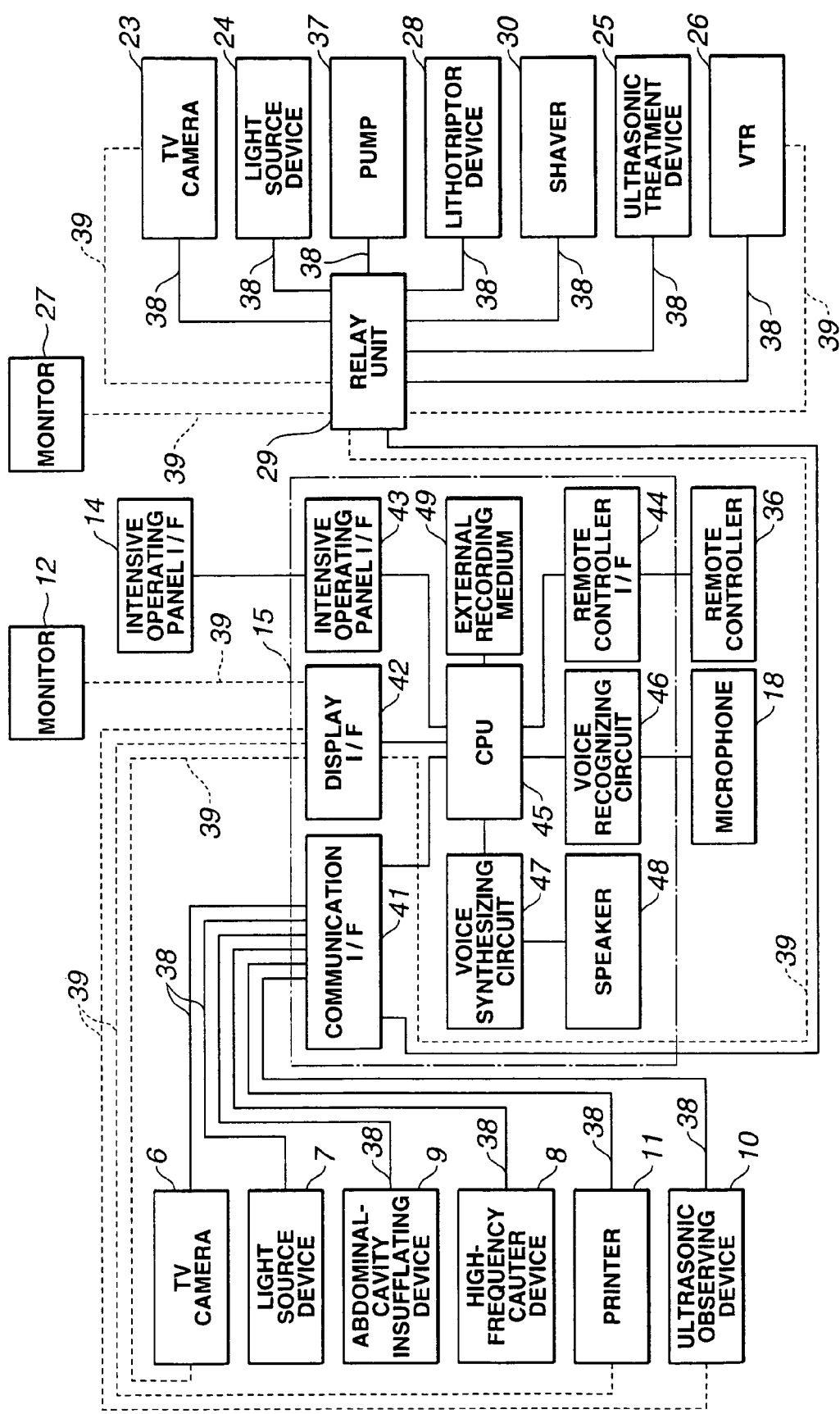

Referring to FIG. 2, the intensive operating panel 14, the remote controller 36, the first TV camera device 6, the first light source device 7, the electric cautery 8, the gas insufflator 9, the printer 11, and the ultrasonic observing device 10 are respectively connected to a communication I/F 41 of the system controller 15 by a communication cable 38 for data transmission and reception. Also, the first monitor 12, the first TV camera device 6, the printer 11, and the ultrasonic observing device 10 are connected to a display I/F 42 of the system controller 15 by a video cable 39, for transmitting and receiving a video signal.

The second TV camera device 23, the second light source device 24, the ultrasonic treatment device 25, the VTR 26, the lithotriptor 28, the shaver 30, and the pump 37 are connected to the relay unit 29 by the communication cable 38 for data transmission and reception. Also, the second monitor 27, the second TV camera device 23, and the VTR 26 are connected to the relay unit 29 by the video cable 39 for transmitting and receiving the video signal.

The relay unit 29 is connected to the system controller 15 by the cable 35 (refer to FIG. 1), is connected to the communication I/F 41 of the system controller 15 via the communication cable 38 in the cable 35, and is connected to the display I/F 42 of the system controller 15 via the video cable 39 in the cable 35.

The system controller 15 comprises: the communication I/F 41; the display I/F 42: a voice recognizing circuit 46 which recognizes a voice signal from the microphone 18; a remote control I/F 44 which transmits and receives data to/from the remote controller 36; a voice synthesizing circuit 47 which synthesizes the voice and generates the voice from a speaker 48; and an intensive operating panel I/F 43 which transmits and receives the data from/to the concentrated operating panel 14, and the circuits are controlled by a CPU 45. An external recording medium 49 can be connected to the system controller 15, and the CPU 45 records and reads the image data to the external recording medium 49.

Figure 3:
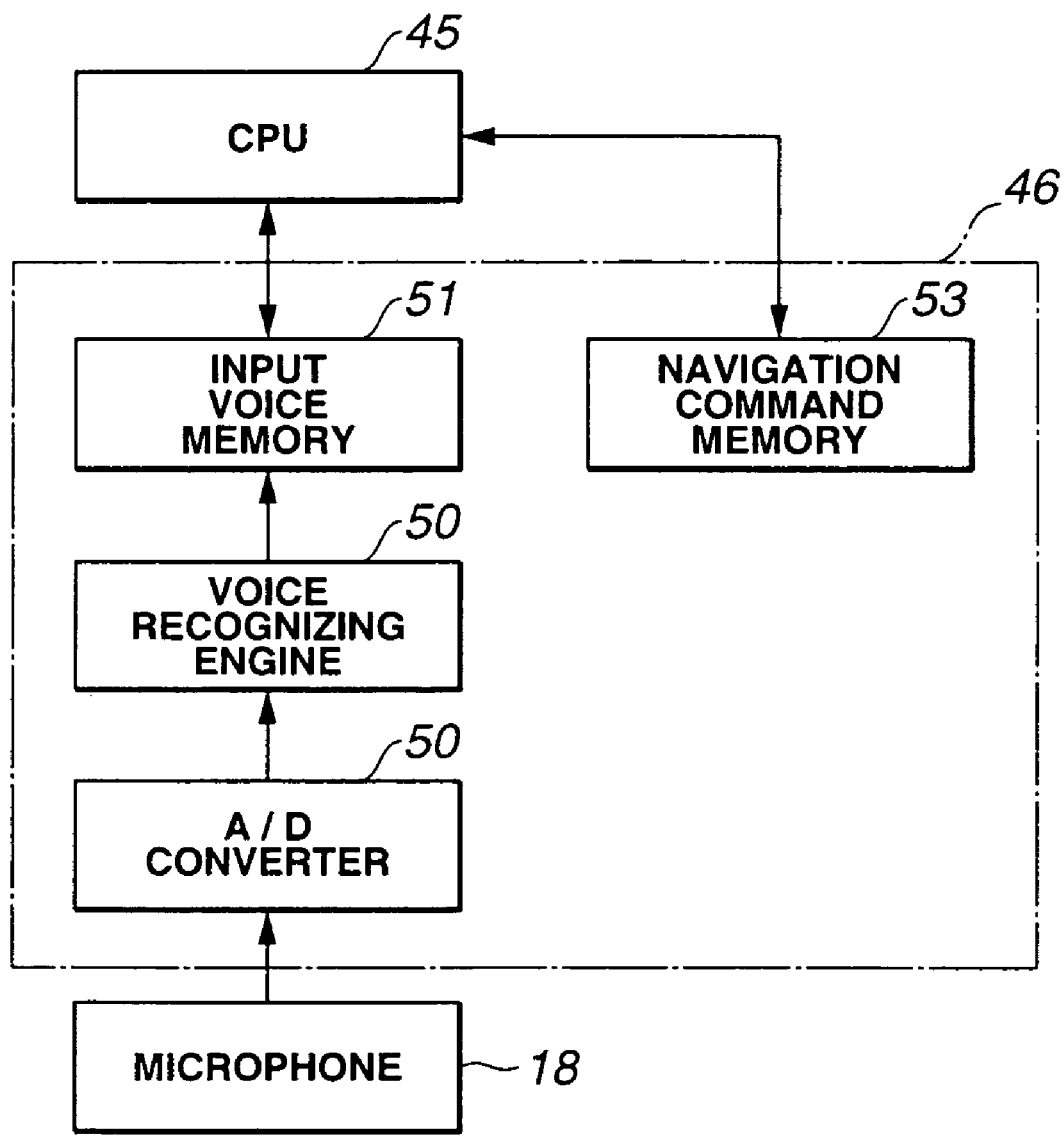

Referring to FIG. 3, the voice recognizing circuit 46 comprises: an A/D converter 51 which A/D converts the voice signal from the microphone 18; a voice recognizing engine 50 which recognizes input voice data A/D converted by the A/D converter 51 and converts the recognized result into character data; an input voice memory 52 which stores the character data; and a navigation command memory 53 which stores navigation command data for comparing whether or not the voice data stored in the input voice memory 52 is predetermined command data by the CPU 45.

The navigation command memory 53 hierarchizes and stores a command on the device, namely, a device command of the electric cautery, the gas insufflator, and the TV camera device, a command on the function, namely, a function command on an output for incision, an output for clotting, air supply, and brightness adjustment, and a command on the operation, namely, an operating command of up/down, start, and stop. The respective commands have a corresponding relationship as shown in Table 1. When the devices are integrated in the single apparatus, the present invention can have the same operation.

TABLE 1

| Command on device | Command on function | Command on operation |
|---|---|---|
| Electric cautery | Output system | Monopolar |
| | | bipolar |
| | Incision mode | Urology |
| | | Mix 1 |
| | | Mix 2 |
| | | Pure |
| | Output for incision | Up |
| | | Down |
| | Clotting mode | Soft |
| | | Soft A |
| | Output for clotting | Up |
| | | Down |
| Gas insufflator | Supply air | Start |
| | | Stop |
| | Set pressure | Up |
| | | Down |
| | Air supply mode | High |
| | | Middle |
| | | Low |
| | Set fluid amount | Up |
| | | Down |
| VTR | Record | Start |
| | | Stop |
| . | . | . |
| . | . | . |
| . | . | . |

The CPU 45 performs the processing for monitoring the character data stored in the input voice memory 52, checks the device command as the monitored result, then, checks the function command corresponding to a predetermined time, and executes the operation of the function of the device corresponding to the case of checking the operating command corresponding to the predetermined time.

Figure 4:
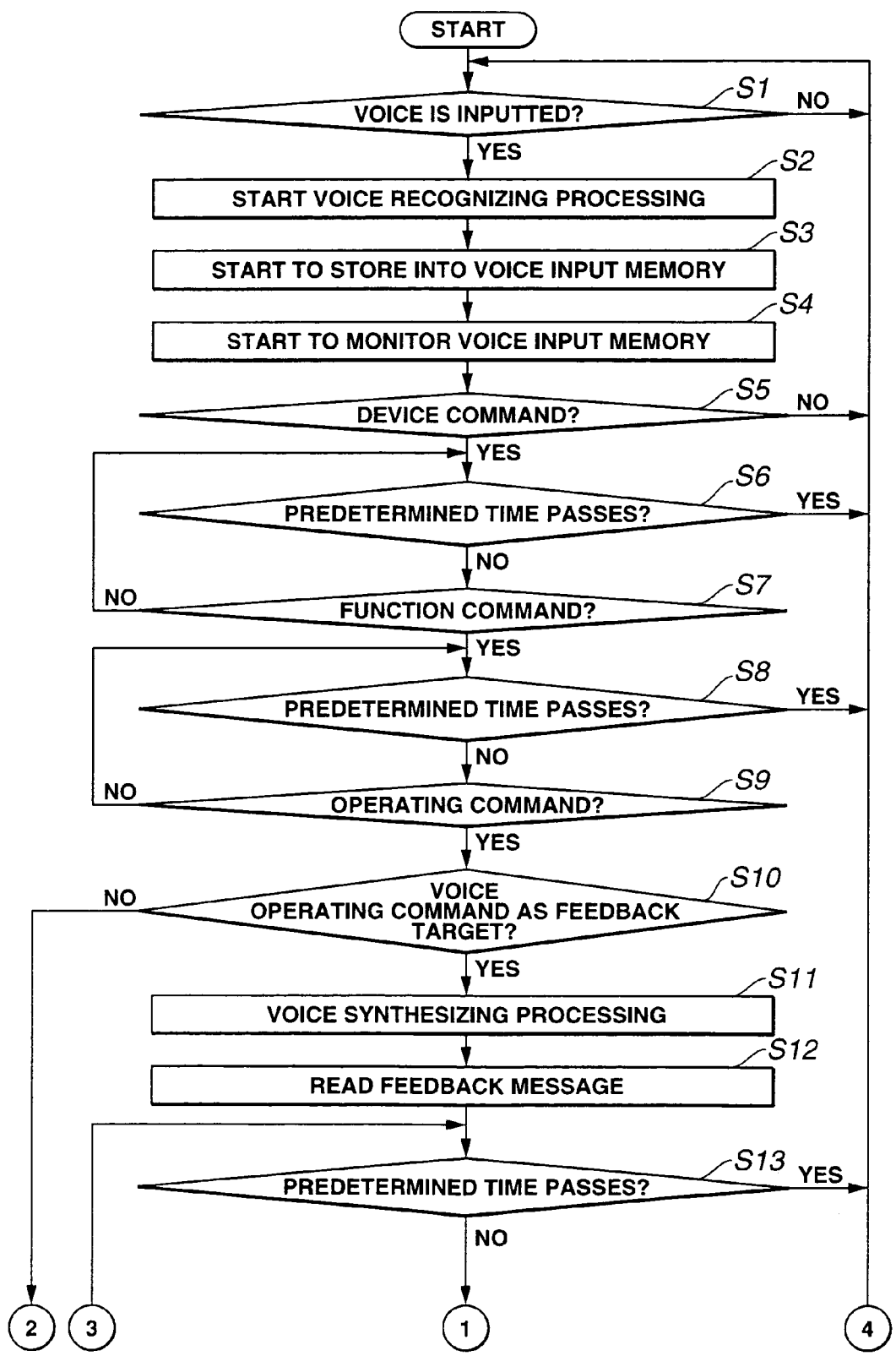
Figure 5:
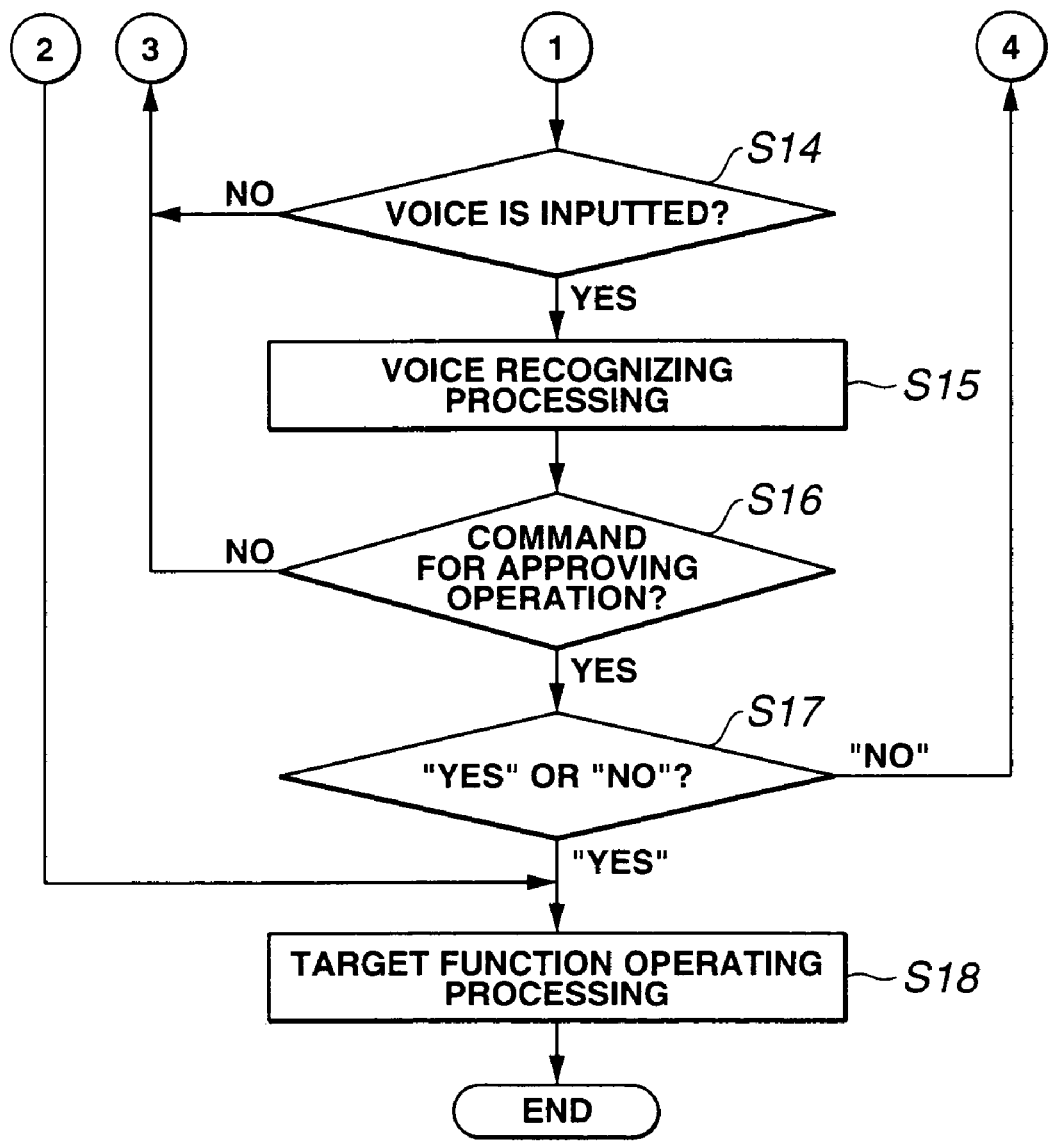

(Operation) Referring to FIGS. 4 and 5, in step S1, the system controller 15 waits for the voice input from the microphone 18. Then, when the voice is inputted, in step S2, the voice recognizing engine 50 starts the processing for converting the voice into character data.

In step S3, the system controller 15 starts to store the character data into the input voice memory 52. In step S4, the CPU 45 starts to monitor the input voice memory 52.

In step S5, the CPU 45 checks the device command. Then, in step S6, the CPU 45 monitors the input voice memory 52 to determine whether or not the function command exists corresponding to the monitored result for the predetermined time.

In step S7, when the corresponding function command is checked, in step S8, the CPU 45 monitors the input voice memory 52 to determine whether or not the operating command exists corresponding to the monitoring result for the predetermined time.

In step S9, it is checked that the corresponding operating command exists, then, in step S10, it is determined whether or not the input voice data is the operating command on the voice as a feedback target.

When it is determined in step S10 that the input voice data is the operating command on the voice as the feedback target, in step S11, the system controller 15 allows the voice synthesizing circuit 47 to synthesize a voice signal for requesting an approval for the feedback processing. In step S12, the speaker 48 reads a feedback message. For example, when the input voice data is the voice operating command as the feedback target indicating "Up output for incision" for the electric cautery, a voice "Is the output for incision up?" as the feedback message is read.

After reading the feedback message, in steps S13 and S14, the voice input is waited for the approval for the predetermined time. If the voice is not inputted for the predetermined time, the processing sequence returns to step S1. If the voice is inputted for the predetermined time, the processing sequence proceeds to step S15.

In step S15, the system controller 15 allows the CPU 45 to compare the input voice data stored in the input voice memory 52 with navigation command data stored in the navigation command memory 53 for the voice recognizing processing. In step S16, it is determined whether or not the input voice data is the command data for approving the operation. If the input voice data is not the command data for approving the operation, the processing sequence returns to step S13. If the input voice data is the command data for approving the operation, the processing sequence proceeds to step S17.

In step S17, it is determined whether the input voice data is the command data for approving the operation indicating "YES" or "NO". If the input voice data is the command data for approving the operation indicating "NO", the processing sequence returns to step S1. If the command data for approving the operation indicating "YES", in step S18, the operating processing for the target function is executed for the operation of the voice operating command as the feedback target to the target device and then the processing ends.

If it is determined in step S10 that the input voice data is not the voice operating command as the feedback non-target, the input voice data is the voice operating command as the feedback non-target. Then, the processing sequence proceeds to step S18 whereupon the target function operating processing is executed for the target device for the operation of the voice operating command as the feedback non-target and then the processing ends.

As a result of the above-mentioned control, when a message "Up the output for the incision of the electric cautery" is vocalized, the up-operation of the electric cautery as the device command, the output for the incision of the corresponding function command, and the corresponding operating command is recognized and the up-operation of the output for the incision of the electric cautery is performed. Thus, the device is operated without discrete voices.

(Advantages)

According to the first embodiment, the convenience is improved because the device is operated by the voice for natural conversation.

Figure 6:
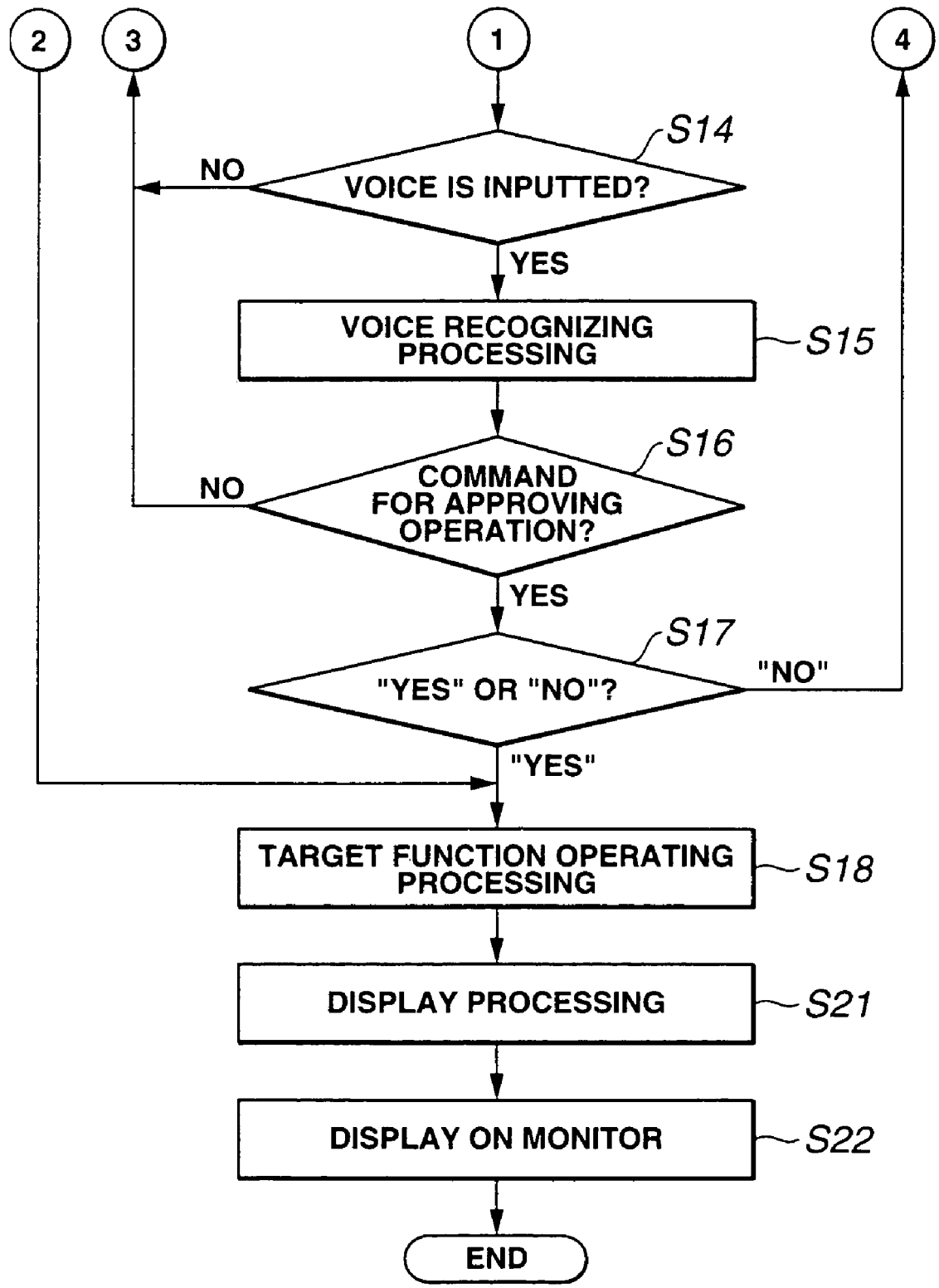

Subsequently to the processing in steps S1 to S16, referring to FIG. 6, in step S21, the display processing is executed to generate information data for displaying information on the voice operating command to the first monitor 12. In step S22, the first monitor 12 displays the endoscope image, command information indicating the contents of voice operating command, and executed result information indicating an executed result of executing the target function operating processing in step S16 and then the processing ends.

Second Embodiment

A second embodiment is substantially the same as that of the first embodiment, therefore, only different portions are described, the same components are designated by the same reference numerals, and a description thereof is omitted.

(Structure and Operation)

Figure 7:
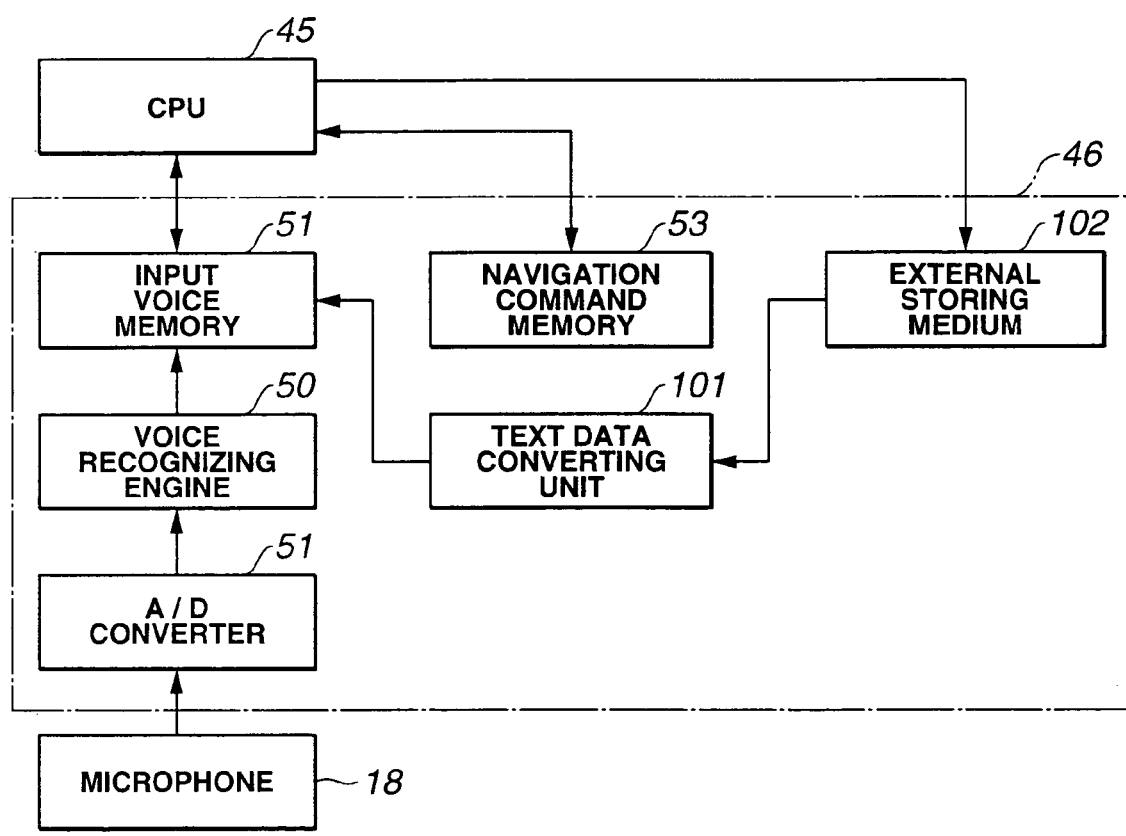
FIGS. 7 and 8 relate to a second embodiment of the present invention.

FIG. 7 shows the voice recognizing circuit 46 according to the second embodiment. The voice recognizing circuit 46 comprises a text data converting unit 101 for converting the character data stored in the input voice memory 52 into text data; and an external storing medium 102 for storing the text data.

Figure 8:
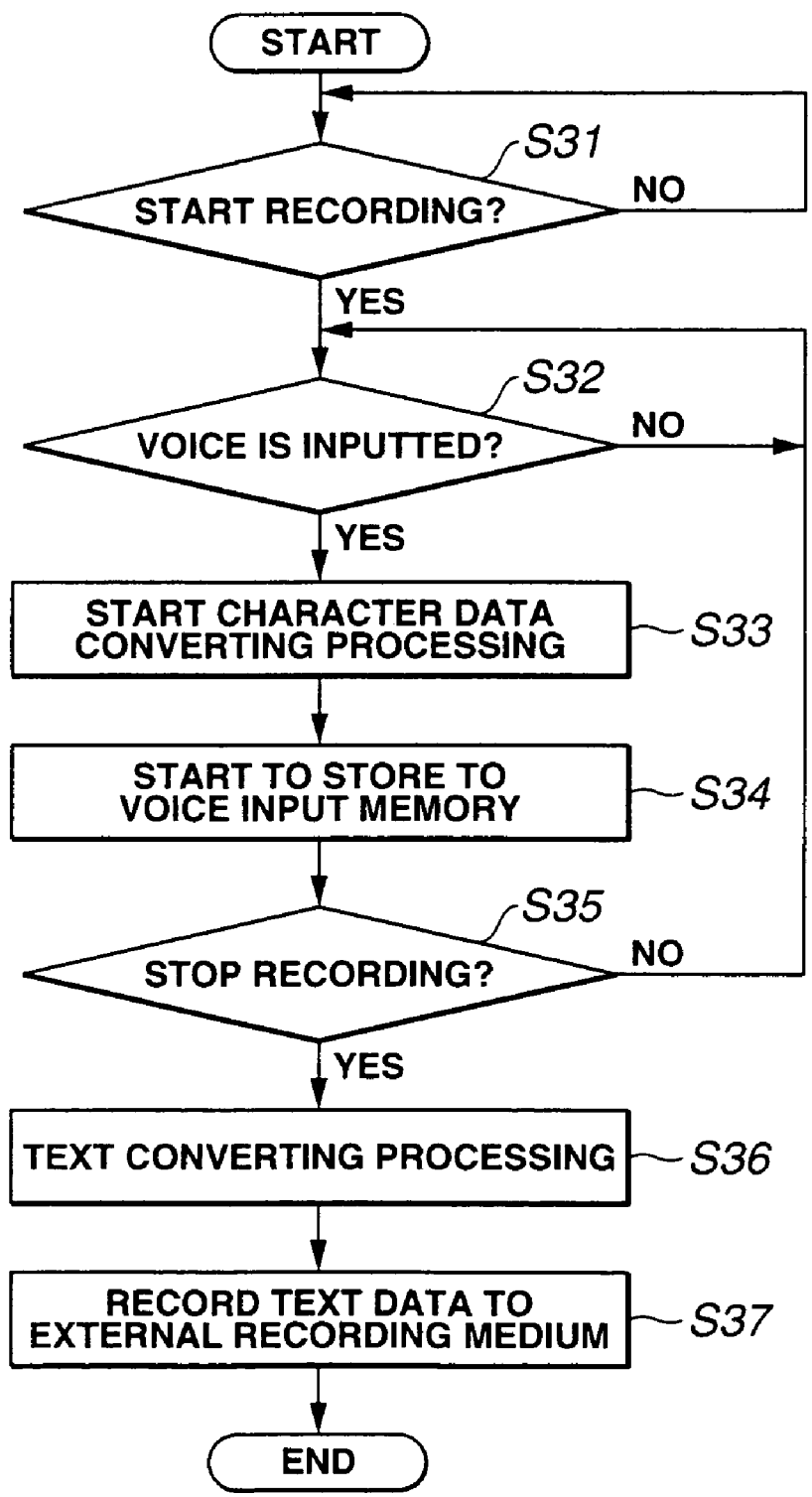

FIG. 8 is a flowchart showing the voice control processing according to the second embodiment. Referring to FIG. 8, in step S31, the system controller 15 waits for the recording start operation by the remote controller 36, the intensive operating panel 14, or the voice operation. After the recording start operation, in step S32, the system controller 15 waits for the voice input from the microphone 18. After inputting the voice, in step S33, the voice recognizing engine 50 starts the processing for conversion into the character data.

In step S34, the character data starts to be stored in the input voice memory 52. In step S35, the system controller 15 waits for the recording stop processing by the remote controller 36, the intensive operating panel 14, or the voice operation. After the recording stop processing, in step S36, the text converting means 49 converts, into the text data, the character data stored in the input voice memory 52.

Then, the system controller 15 performs the processing for recording the text data converted in step S37 to the external storing medium 102.

(Advantages)

According to the second embodiment, in addition to the advantages according to the first embodiment, the data is automatically recorded without recording the history on the operation and the commands during the operation. Thus, the convenience is improved.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

The invention claimed is:

1. An endoscope system comprising:
   a voice input unit which inputs voice in a natural phrase;
   a voice and character converting means which recognizes the voice inputted and converts the inputted voice into character data;
   comparison data storing means for prestoring, as comparison data with a hierarchal structure, first command character trains for specifying each of a plurality of devices in a storage area corresponding to a first hierarchal tier in a memory in a system controller for controlling the plurality of devices, second command character trains related to respective functional commands of the plurality of devices in a storage area corresponding to a second hierarchal tier branching from the first hierarchal tier, and third command character trains related to respective operational commands of the functional commands in a storage area corresponding to a third hierarchal tier branching from the second hierarchal tier;
   a monitoring unit which monitors the first, second and third command character trains that are stored in the comparison data storing means and the character data that is converted by the voice and character converting means;
   an executing unit which executes an instruction previously allocated to the combination of the command character trains that correspond to the first, second and third command character command trains, upon detecting, in the converted character data, the command character train from the first, second and third command character trains for a predetermined time interval in accordance with the hierarchal structure of the preset comparison data; and
   a verification requesting means for issuing an audible verification request when the instruction is predetermined to require verification prior to execution.

2. The endoscope system according to claim 1, wherein the plurality of devices comprise an electric cautery device.

3. The endoscope system according to claim 2, wherein the command character trains include character trains which designate a plurality of output formats of the electric cautery device.

4. The endoscope system according to claim 3, wherein the character trains which designate the plurality of output formats of the electric cautery device include an output system designating group, an incision mode designating group, an incision output designating group, a clotting mode designating group, and a clotting output designating group.

5. The endoscope system according to claim 4, wherein the plurality of devices further include a gas insufflator.

6. The endoscope system according to claim 5, wherein the command character trains include character trains which designate a plurality of output formats of the gas insufflator.

7. The endoscope system according to claim 6, wherein the character trains which designate the plurality of output formats of the gas insufflator include an air-supply on/off designating group, a set pressure designating group, an air-supply mode designating group, and a set fluid amount designating group.

8. The endoscope system according to claim 1, wherein the plurality of devices include a gas insufflator.

9. The endoscope system according to claim 8, wherein the command character trains include character trains which designate a plurality of output formats of the gas insufflator.

10. The endoscope system according to claim 9, wherein the character trains which designate the plurality of output formats of the gas insufflator include an air-supply on/off designating group, a set pressure designating group, an air-supply mode designating group, and a set fluid amount designating group.

11. The endoscope system according to claim 1, wherein the executing unit executes the instruction allocated to the combination of the command character trains and thereafter displays the executed result of the instruction.

12. A device control method comprising:
   a voice input step of inputting voice in a natural phrase;
   a voice and character converting step of recognizing the voice inputted and converting the inputted voice into character data;
   a comparison data storing step for prestoring, as comparison data with a hierarchal structure, first command character trains for specifying each of a plurality of devices in a storage area corresponding to a first hierarchal tier, second command character trains related to respective functional commands of the plurality of devices in a storage area corresponding to a second hierarchal tier branching from the first hierarchal tier, and third command character trains related to respective operational commands of the functional commands in a storage area corresponding to a third hierarchal tier branching from the second hierarchal tier;
   a monitoring step of monitoring the first, second and third command character trains that are stored in the comparison data storing step and the character data that is converted by the voice and character converting step;
   an executing step of executing an instruction previously allocated to the combination of the command character trains that correspond to the first, second and third command character trains, upon detecting, in the converted character data, the command character train from the first, second and third command character trains for a predetermined time interval in accordance with the hierarchal structure of the preset comparison data; and
   a verification requesting step for issuing an audible verification request when the instruction is predetermined to require verification prior to execution.

13. The device control method according to claim 12, further comprising: a display step of displaying an executed result of the instruction after executing the instruction allocated to the combination of the command character trains in the executing step.

14. An endoscope system comprising one or a plurality of devices, the endoscope system comprising:
   voice input means which inputs voice in a natural phrase;
   voice and character converting means which recognizes the voice inputted and converts the inputted voice into character data;
   a system controller which controls the plurality of devices;
   comparison data storing means for prestoring, as comparison data with a hierarchal structure, first command character trains for specifying each of a plurality of devices in a storage area corresponding to a first hierarchal tier in a memory in a system controller for controlling the plurality of devices, second command character trains related to respective functional commands of the plurality of devices in a storage area corresponding to a second hierarchal tier branching from the first hierarchal tier, and third command character trains related to respective operational commands of the functional commands in a storage area corresponding to a third hierarchal tier branching from the second hierarchal tier;
   monitoring means which monitors the first, second and third command character trains that are stored in the comparison data storing means and the character data that is converted by the voice and character converting means; and executing means which executes an instruction previously allocated to the combination of the command character trains that correspond to the first, second and third command character trains, upon detecting, in the converted character data, the command character train from the first, second and third command character trains for a predetermined time interval in accordance with the hierarchal structure of the preset comparison data.

* * * * *